United States Patent [19]

Groeger et al.

[11] Patent Number: 4,957,109
[45] Date of Patent: Sep. 18, 1990

[54] ELECTROCARDIOGRAPH SYSTEM

[75] Inventors: Jeffrey Groeger, Bardonia; Saul Miodownik, W. Hempstead, both of N.Y.

[73] Assignee: Cardiac Spectrum Technologies, Inc., Bardonia, N.Y.

[21] Appl. No.: 234,982

[22] Filed: Aug. 22, 1988

[51] Int. Cl.$^5$ ............................................. A61B 5/04
[52] U.S. Cl. ........................................ 128/640; 128/696; 128/901
[58] Field of Search ............... 128/639, 640, 641, 644, 128/695, 696, 783, 798, 799, 802, 901

[56] References Cited

U.S. PATENT DOCUMENTS

| | | | |
|---|---|---|---|
| 770,014 | 9/1904 | Linn | 128/802 |
| 3,409,007 | 11/1968 | Fuller | 128/644 |
| 3,534,727 | 10/1970 | Roman | 128/644 |
| 3,623,477 | 11/1971 | Trent | 128/644 |
| 4,016,868 | 4/1977 | Allison | 128/644 |
| 4,121,573 | 10/1978 | Crovella et al. | 128/640 |
| 4,121,575 | 10/1978 | Mills | 128/644 |
| 4,122,843 | 10/1978 | Zdrojkowski | 128/644 |
| 4,353,372 | 10/1982 | Ayer | 128/640 |
| 4,381,012 | 4/1983 | Russek | 128/644 |
| 4,409,983 | 10/1983 | Albert | 128/690 |
| 4,425,921 | 1/1984 | Fujisaki et al. | 128/644 |
| 4,572,197 | 2/1986 | Moore et.al. | 128/644 |
| 4,580,572 | 4/1986 | Granek et al. | 128/644 |
| 4,583,547 | 4/1986 | Granek et al. | 128/644 |
| 4,608,987 | 9/1986 | Mills | 128/644 |
| 4,635,642 | 1/1987 | Cartmell et al. | 128/639 |
| 4,763,660 | 8/1988 | Kroll et al. | 128/798 |

*Primary Examiner*—Randall L. Green
*Assistant Examiner*—Randy Shay
*Attorney, Agent, or Firm*—Sprung Horn Kramer & Woods

[57] ABSTRACT

An electrode assembly for acquiring physiological signals, comprising a flexible substrate having a bottom surface and a top surface, means forming a plurality of electrodes at the bottom surface of the substrate and each electrode having a bottom surface facing away from the substrate, an electrical connector fixed to the substrate and having a plurality of connector elements, a plurality of flexible conductors fixed on the substrate and connecting the electrodes to the connector elements, a layer of conductive adhesive on the bottom surface of each electrode; and an adhesive layer on at least a portion of the bottom surface of the substrate.

7 Claims, 5 Drawing Sheets

ELECTROCARDIOGRAPH SYSTEM

BACKGROUND OF THE INVENTION

The present invention relates to electrocardiographic systems and in particular to electrode assemblies for receiving physiological signals, and the interface circuitry which takes the signal from the electrode assembly and applies it to diagnostic and display devices such as an electrocardiograph or a display monitor.

Current systems of this type do not allow patients freedom to move, since the patient is tethered to monitors. Moreover, the interface circuitry used in current systems do not lend themselves to use in recovery rooms and critical care facilities wherein multiple units are present and where the running of numerous wires to connect the various patients to the monitors is undersirable and dangerous.

SUMMARY OF THE INVENTION

The main object of the present invention is to eliminate the disadvantages of current electrode assemblies and electrocardiographic systems.

Another object of the present invention is to provide a reusable and disposable self-contained EKG electrode system. The system is implimented as a hard wired or telemetry device that is positioned to automatically acquire a standard 12 lead diagnostic electrocardiogram or multiple leads for intraoperative or intensive care cardiac monitoring, or ambulatory and home monitoring.

In accordance with the invention, the device comprises flexible screen printed circuits that conform to human body contour. The flexible printed circuits can be disposed directly on the body or can be incorporated within a vest. Within the outline of the device are located adhesive conductive patches that serve to secure the electrodes as well as provide electrical connection for the individual electrodes.

The device can also incorporate sensors which acquire heart sounds, transcutaneous pulse oximetry, respiratory rate and skin temperature, etc. The addition of these items will allow the device to be used for neonatal monitoring, fetal monitoring during pregnancy and nocturnal apnea monitoring for adults sleep apnea syndrome and infants at high risk of Sudden Infant Death.

The physiological signals that are acquired in this manner are either hard wired to existing monitoring equipment at a single connection point or alternatively attached to a miniature telemetry device with power provided by batteries incorporated within the electrode system. The telemetry unit, using infrared technology transmits to a receiver either by wireless or fiber optics, which receiver adapts to existing monitoring devices. The telemetry system will have the capacity to use standard electrodes which can be adapted through a separate disposable battery power adapter.

The telemetry system according to the present invention allows patients freedom of movement without being tethered to existing monitors. It offers great promise for cardiac monitoring during stress testing, in the operating room, in intensive care and cardiac care units and when a patient must be left unattended such as during a diagnostic radiologic examination or when receiving a radiation treatment.

Interfacing the transmitter to an electrocardiogram machine would allow instantaneous recording of multiple ECG's without a technician and standardized electrode placement.

These and other features and advantages of the present invention will be seen from the following detailed description of the invention taken with the attached drawings, wherein:

BRIEF DESCRIPTION OF THE DRAWINGS

FIG. 2b is a sectional view of the electrode of FIG. 2a;

DETAILED DESCRIPTION OF THE INVENTION

Figure 1:
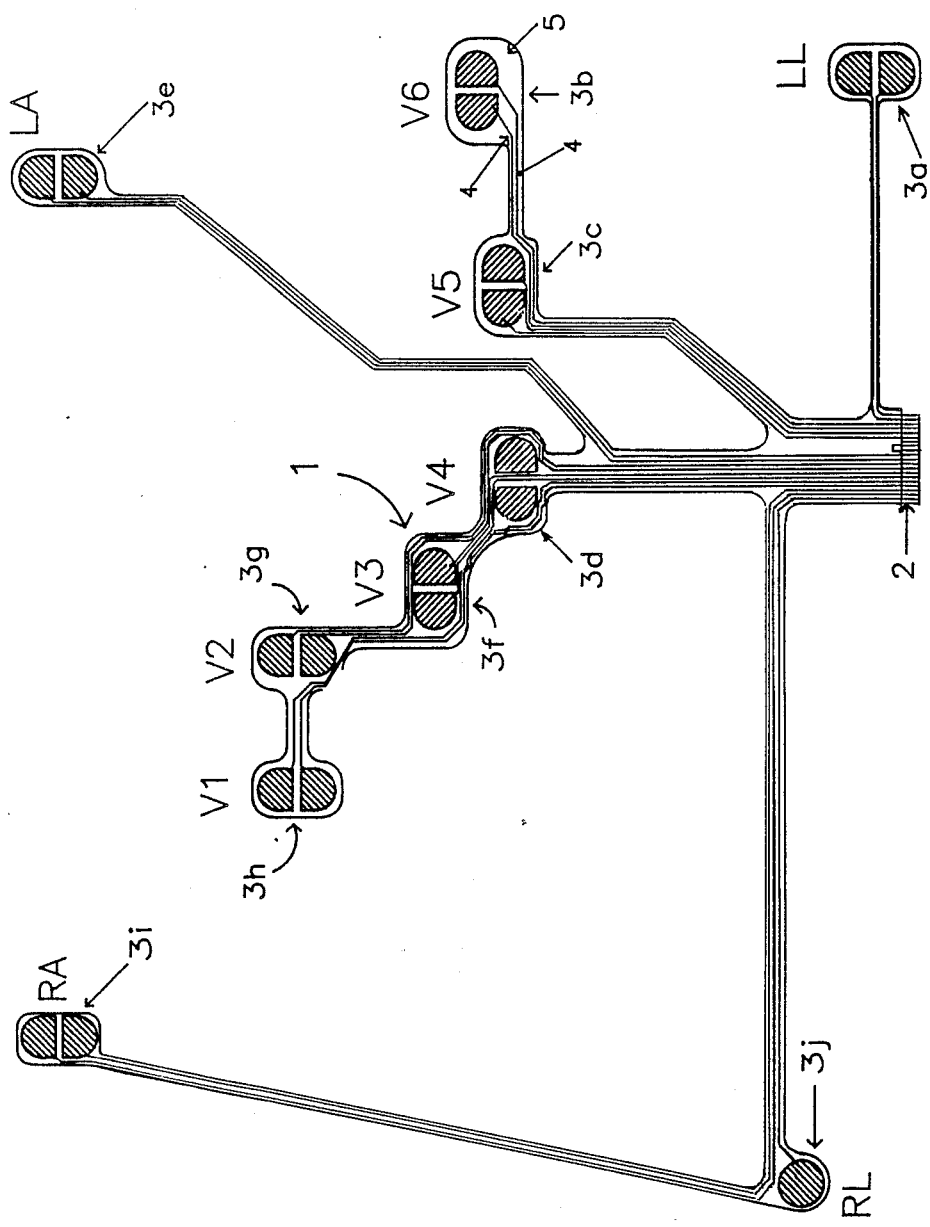
FIG. 1 is a top view of the electrode assembly according to the present invention.

FIG. 1 illustrates the electrode assembly 1 according to the present invention. The electrode assembly comprises a substrate 5 of flexible circuit board material such as mylar, kapton or polyester and which is electrically nonconductive. Disposed on the bottom surface of the substate are a plurality of electrodes 3a–3j which are predeterminately spaced so as to be disposed at desired points on a human body during an electrocardiogram. The electrodes 3a–3i are connected to a connector 2 via conductors 4.

Figure 2A:
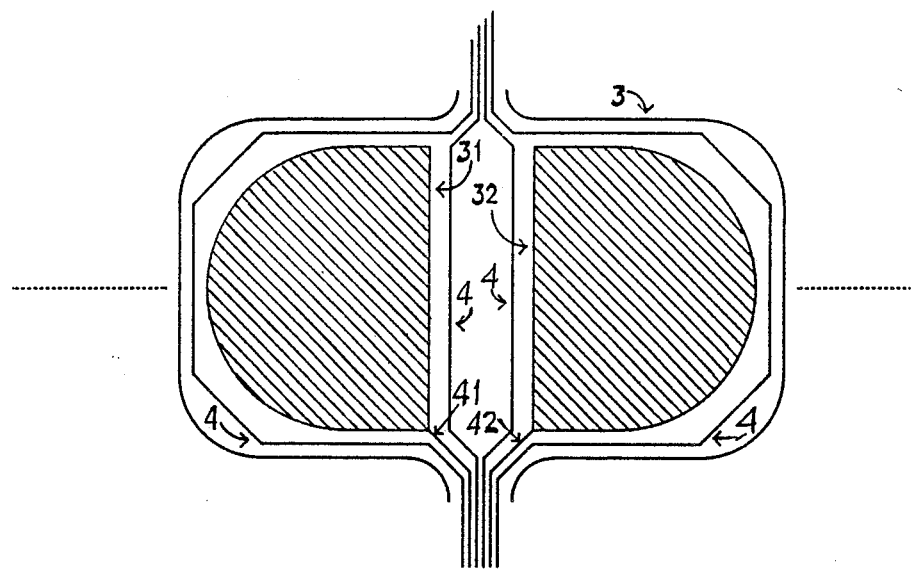
FIG. 2a is an enlarged view of one electrode according to the present invention.

FIG. 2a shows an enlarged view of any one of electrodes 3a–3i and is labeled as electrode 3 and comprises two sections 31, 32 which are conductive sensing regions and which have separate conductors 41 and 42 traveling to connector 2. As can be seen, other interconnecting conductors 4 are disposed between and around the sensing regions 31 and 32.

Figure 2B:
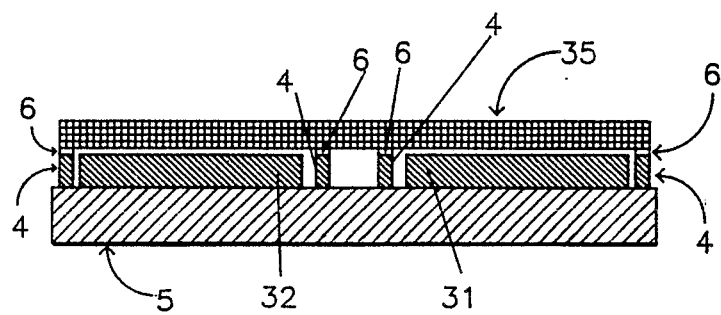

As can be seen from FIG. 2b, the conductors 4 have dielectric material 6 thereover to prevent any shorting of the conductors. Also disposed over the sensing regions 31 and 32 is a layer of hydrogel 35 which is a conductive adhesive which is used to maintain the electrode in place and to provide better conduction.

The bottom surface of the substrate also includes a nonconductive adhesive layer 8 (FIG. 2c) at selected portions thereof in order to maintain the electrode assembly in place on the human body during use.

The electrodes 3 with the two sensing regions 31 and 32 are effectively used to cancel noise occurring at the site of the electrode by feeding the signals from conductors 41 and 42 into a substracting circuit which will subtract the two signals from each other so that the resulting difference signal has any noise on the signal cancelled therefrom. This circuitry will be described hereinafter.

Figure 2C:
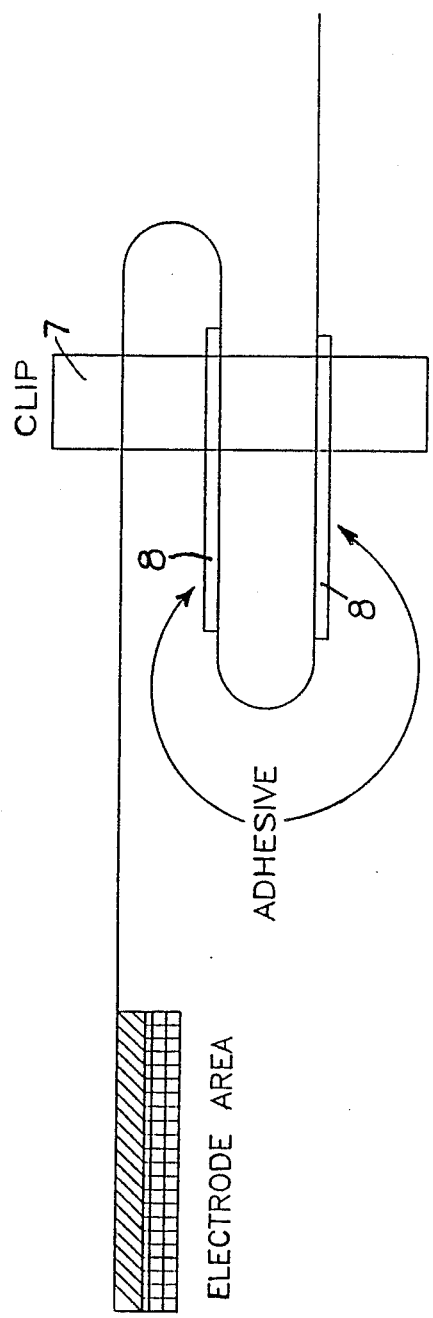
FIG. 2c is a sectional view of another feature of the electrode assembly according to the present invention.

In those situations where the user has a smaller torso and thus the elongated lengths of conductor need to be adjusted, the electrode assembly 1 can be provided with clips 7 shown in FIG. 2c in which the flexible substrate is folded into an S. The clip can then provide for an adjustable length of the assembly when disposed on a patient.

FIG. 1 also has the functional signal names for each of the electrodes as utilized in the 12 lead electrocardiogram convention.

These signals are then utilized in the circuitry of FIGS. 3 and 4 as will now be discussed.

Figure 3:
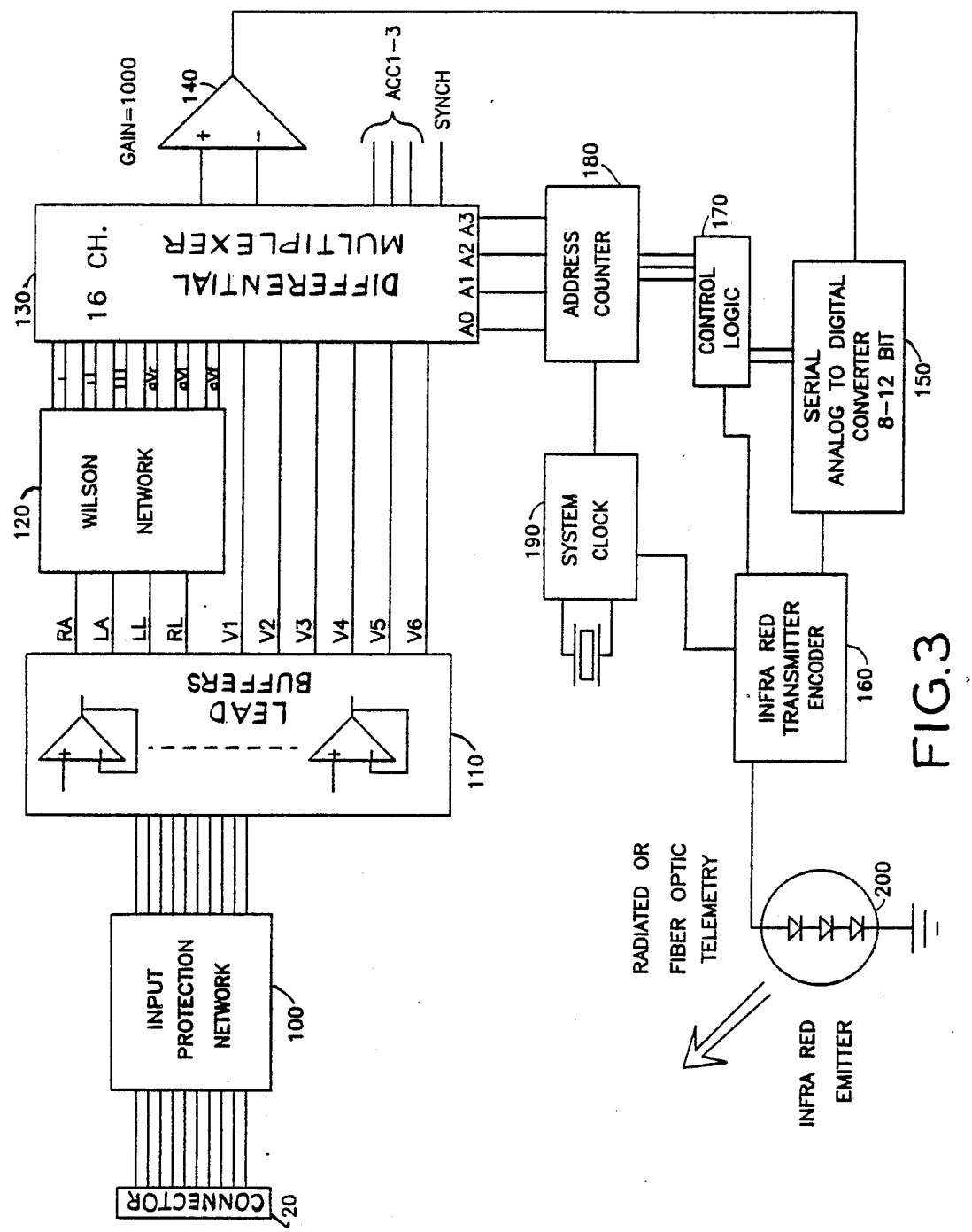
FIGS. 3 and 4 are schematic diagrams of the circuitry for use in the electrocardiograph system according to the present invention.

As shown in FIG. 3, the connector 2 mates with connector 20 and the signals therefrom are first applied to an input protection network 100 which is for example a phototransistor and photoreceiver circuit which isolates the electrode assembly on the body of the user from the circuitry and voltages downstream of the input protection network.

The outputs from the input protection network is fed to a lead buffer circuit 110 which shapes the signals for further processing.

The signals from the lead buffers 110 are fed in part to a Wilson network 120 which is a conventional resistor network which creates six of the signals used for electrocardiography. The six Wilson signals and the other six signals taken directly from the lead buffers 110 are applied to a 16 channel differential time multiplexer 130 which multiplexes these 12 lead signals as well as four control signals.

The multiplexing of the signals is carried out under the control of system clock 190 which feeds its output to an address counter 180 which in turn generates the four address bits needed to define the 16 channels of multiplexing. The counter 180 also provides control signals for control logic 170 which controls the infrared transmitter encoder 160 and the serial analog to digital converter 150 so that the timing thereof is synchronized with the differential multiplexer and the system clock.

The single line multiplexed signal from multiplexer 130 is fed into amplifier 140 to increase the gain by a factor of 1000 and the output of the amplifier 140 is fed to a serial to analog to digital converter wherein a serial digital data stream is produced and fed to an infrared transmitter encoder 160. The infrared transmitter encoder 160 feeds the output to an infrared emitter 200. The output of the infrared emitter can either be transmitted as a wireless transmission signal or through a fiber optic cable (not shown) in a conventional manner.

Figure 4:
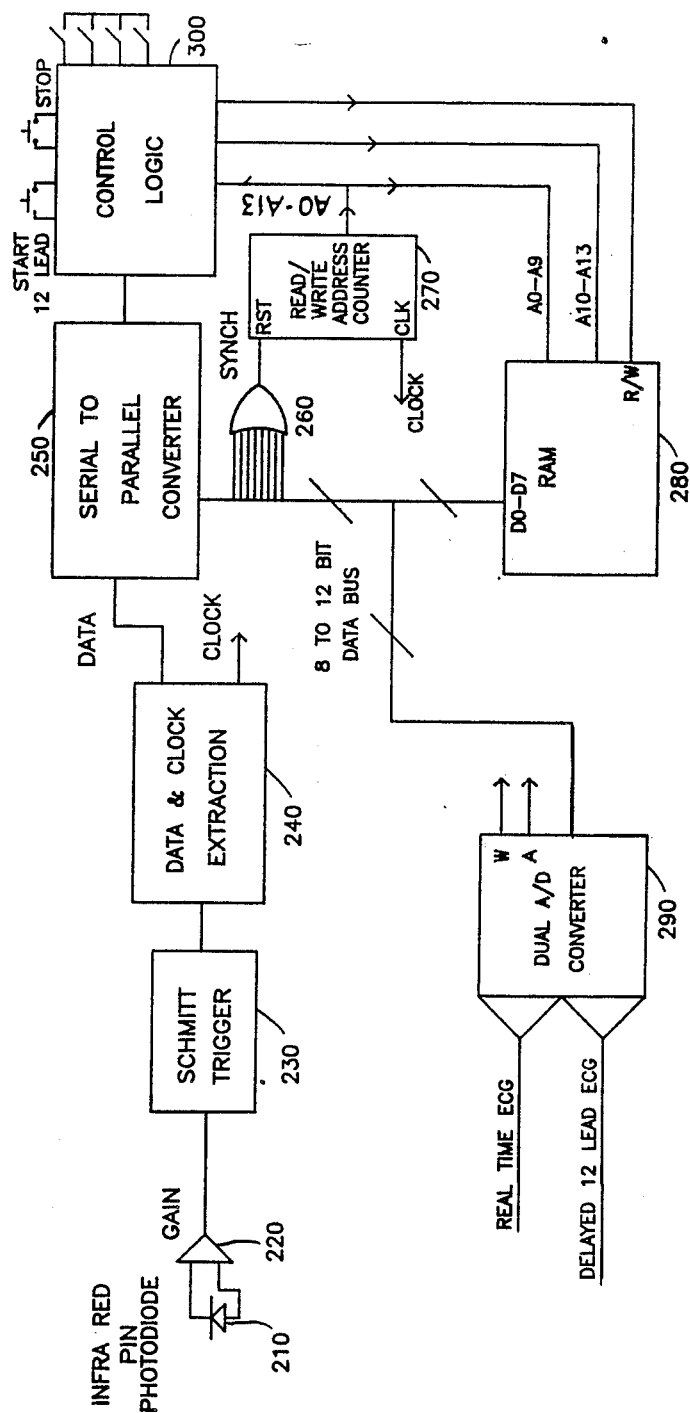

In FIG. 4, a PIN infrared photodiode receiver 210 receives the wireless transmitted infrared signal or the output from a fiber optic cable and this digital signal is then fed to an amplifier 220 to increase the gain thereof and to a Schmidt trigger 230 to reshape the waveform. The digital signal from the Schmidt trigger 230 is fed to a data and clock extraction network 240 which extracts the four control signals multiplexed into the single line signal in multiplexer 130 so that the control signals can be used to synchronize the following circuitry to the transmitted signal and the data signal can be fed to a serial to parallel converter 250 to obtain the 12 individual digital signals.

The 12 signals are then fed in parallel to a 16 K by 8 to 12 bit RAM 280 and at the same time to a dual digital to analog converter 290. A synchronizing signal obtained from gate 260 and the control signals from extracting circuit 240 are fed to a read write address counter 270 which controls the ram 280 to effect storage of the signals therein.

A control logic circuit 300 is also provided which controls the RAM 280 and the dual digital to analog converter 290 so as to effect a desired output from the dual digital to analog converter 290 of either the real time ECG signal or the real time ECG signal along with a delayed 12 lead ECG signal which has been obtained from memory 280.

In this way, one viewing a monitor of a patient's ECG signal, can see the real time signal as well as replay of a previous signal so that the two can be compared or otherwise analyzed to obtain vital information about the patient.

It will be appreciated that the instant specification and claims are set forth by way of illustration and not limitation, and that various modifications and changes may be made without departing from the spirit and scope of the present invention.

What is claimed is:

1. An electrode assembly for receiving physiological signals, comprising:
   a flexible substrate comprising a first section disposable over the heart and at least three elongated sections extending from the first section having a bottom surface and a top surface;
   means forming a plurality of electrodes at the bottom surface of the substrate at the first section and the elongated sections and each electrode having a bottom surface facing away from the substrate;
   an electrode connector fixed to the substrate and having a plurality of connector elements;
   a plurality of flexible conductors fixed on the substrate and connecting the plurality of electrodes to the connector elements;
   means for adjusting the length of at least one of the three elongated sections of the substrate and the conductors fixed thereto comprising means for releasably retaining the at least one elongated section folded on itself;
   a layer of conductive adhesive on the bottom surface of each electrode; and
   an adhesive layer on at least a portion of the bottom surface of the substrate.

2. The electrode assembly according to claim 1, wherein the means forming the plurality of electrodes comprises for each electrode two aligned spaced apart electrode faces each connected to a different conductor.

3. The electrode assembly according to claim 2, further comprising circuit means connected to the connector elements and receptive of the physiological signals from the plurality of electrodes to produce 12 lead signals therefrom comprising means for subtracting the signals of the two faces of each electrode from each other to obtain a difference signal with low noise and means receptive of each difference signals for producing the 12 lead signals.

4. The electrode assembly according to claim 3, wherein the circuit means further comprises means for time multiplexing the 12 lead signals onto a single signal line.

5. The electrode assembly according to claim 4, wherein the circuit means further comprises wireless transmitting means receptive of the time multiplexed signals for transmitting same to a remote receiver.

6. The electrode assembly according to claim 1, wherein the means for releasably retaining comprises a clip for releasably holding at least one elongated section in an S-shaped fold.

7. An electrode assembly for receiving physiological signals, comprising: a first electrode having a single face; a plurality of second electrodes, each comprising two side-by-side spaced apart electrode faces; and circuit means receptive of signals from each second electrode for subtracting signals at the two side-by-side faces to obtain a difference signal representing only noise.

* * * * *